United States Patent [19]

Barouk

[11] Patent Number: 4,726,127
[45] Date of Patent: Feb. 23, 1988

[54] SHOE WITH HEEL SUPPORT AND WITH MINIMUM CONTACT FOR THE BALL OF THE FOOT, PARTICULARLY FOR USE AFTER SURGERY OR TRAUMA

[76] Inventor: Louis S. Barouk, Chemin de la Roche, 33370 Tresses, France

[21] Appl. No.: 909,939

[22] Filed: Sep. 22, 1986

[30] Foreign Application Priority Data

Jun. 9, 1986 [EP] European Pat. Off. ....... 86 401238.0

[51] Int. Cl.$^4$ ............................................. A43B 7/00
[52] U.S. Cl. .......................................... 36/110; 36/81; 128/83.5
[58] Field of Search ................ 36/110, 81, 11.5, 92, 36/96, 7.5; 128/83.5, 83

[56] References Cited

U.S. PATENT DOCUMENTS

| | | | |
|---|---|---|---|
| 2,725,648 | 12/1955 | Kirk et al. | 128/83.5 |
| 4,370,818 | 2/1983 | Simoglou | 36/110 X |
| 4,446,856 | 5/1984 | Jordan | 128/83.5 X |
| 4,546,557 | 10/1985 | Barouk et al. | 36/110 |
| 4,677,767 | 7/1987 | Darby | 36/110 X |

FOREIGN PATENT DOCUMENTS

| | | | |
|---|---|---|---|
| 2611973 | 9/1977 | Fed. Rep. of Germany | 128/83.5 |
| 2097294 | 3/1972 | France | 36/110 |

*Primary Examiner*—James Kee Chi
*Attorney, Agent, or Firm*—Roylance, Abrams, Berdo & Goodman

[57] ABSTRACT

The present invention concerns a shoe, particularly for post-surgery or post-trauma use, intended to be worn by a patient whose ball of the foot is suffering from an injury or from any sort of damage which may be painful, this shoe comprising an upper (1) which is integral with a block sole (2) of which the posterior part is constituted of a heel (3) which is substantially thicker at the front than at the back.

In the invention, the block sole (2) comprises a thin anterior part (4) which extends the top part of the heel forward with the same inclination as the latter and which presents larger crosswise and lengthwise dimensions than those of the foot (P). This thin anterior part (4) is practically indeformable lengthwise and crosswise, but can flex in its height in an area (A) situated essentially at the point of the Lisfranc division of the foot, without coming into contact with the ground.

12 Claims, 5 Drawing Figures

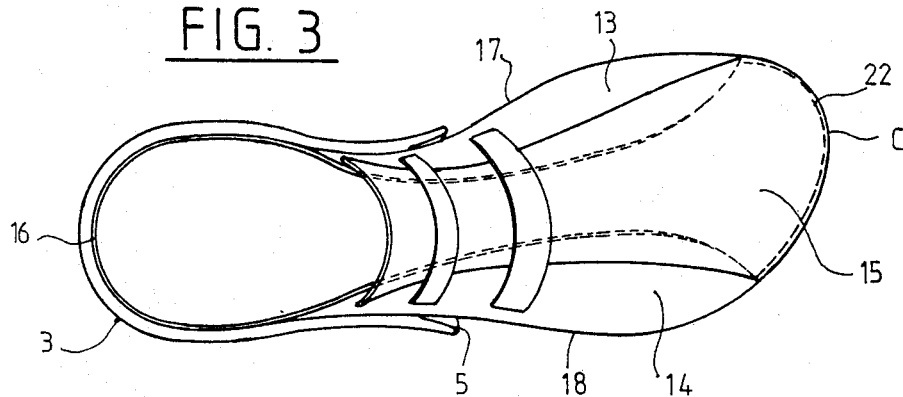
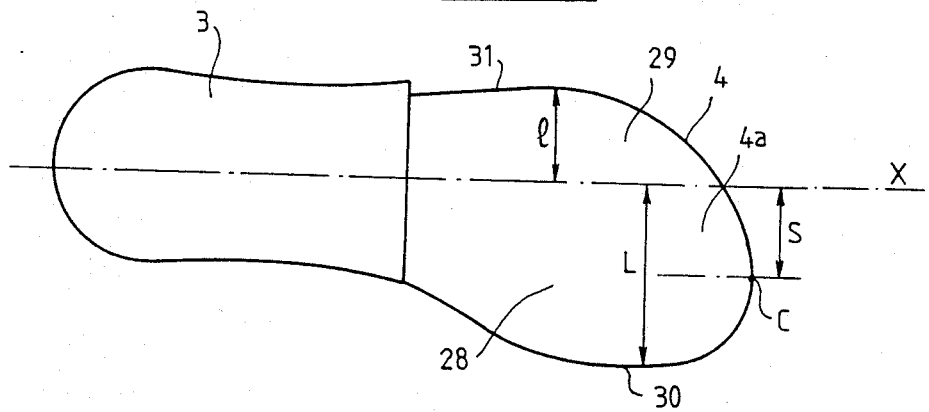
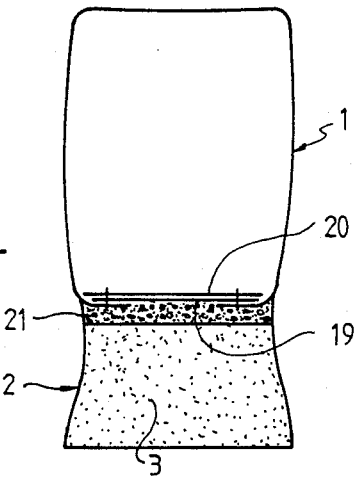

SHOE WITH HEEL SUPPORT AND WITH MINIMUM CONTACT FOR THE BALL OF THE FOOT, PARTICULARLY FOR USE AFTER SURGERY OR TRAUMA

The present invention relates to a shoe, particularly for use after surgery or trauma, to be worn by a patient whose ball of the foot or fore-foot has been harmed or has been subject to any damage, making any external contact of said ball of the foot, in particular contact with the ground, painful or harmful, this shoe comprising an upper which is integral with a block sole of which the posterior part is constituted of a heel which is substantially thicker at the front than at the back, thus determining an upward and forward inclination of the top part of the heel.

Existing shoes of this type for example can be worn by a patient whose ball of the foot has been subjected to surgery or is oedemic, inflamed, wounded or the like.

In such cases, these shoes in fact hold the foot at a slight slope, to prevent any painful contact of the ball of the foot with the ground, thus allowing the patient to walk almost normally, without constraining and uncomfortable use of canes, crutches or walking casts.

However, shoes of this type, presently commercially available, are completely truncated at the front so that the ball of the foot entirely extends to the outside without any external contact or support, and it has been proven that this is the source of certain drawbacks during usage.

In the first place, in such truncated shoes, the ball of the foot is exposed to anterior and lateral shocks which not only cause great pain, but also, in the case of a post-surgical use of the shoe, may cause a break of the osteosynthesis materials.

Other drawbacks of these known shoes consist in the poor positioning of the ball of the foot, which, in some subjects, can cause contractures with dorsal or plantar flexion of the toes, in the possibility of an anterior imbalance in the course of walking, especially perceptible in aged persons, and in the risks of the appearance of plantar pains upon contact with the anterior edge of the inner sole of the open shoe. Besides, it has been established that the total absence of support of the ball of the foot was the cause of trophic troubles.

The present invention proposes to remedy all of these drawbacks, and, to do this, the object is a shoe of the type specified in the preamble, characterized in that its block sole also comprises a thin anterior part which extends the top part of the heel forward while preserving the same inclination as the latter, said thin anterior part having greater crosswise and lengthwise dimensions than the corresponding dimensions of the foot and being practically indeformable lengthwise and crosswise, but flexible in height in an area situated essentially at the point of the Lisfranc division of the foot, and the dimensions of the the of the block sole and the degree of flexibility of the thin anterior part are also determined as a function of the dimensions of the foot to be shod, to prevent any contact of said anterior part with the ground when standing upright or while walking.

Accordingly, the post-surgical or post-trauma shoe according to the present invention is provided with protection at the ball of the foot against anterior and lateral impacts, while still preserving the properties of presently used shoes, in other words holding the foot at a slope, by virtue of which the ball of the foot remains without any contact with the ground during walking. Contrary to traditional shoes, the end of the block sole need not be provided with a wear pad.

The thin anterior part (corresponding to the camber and to the pad of a traditional shoe), which assures this protection against shocks as a result of larger lengthwise and transverse dimensions, is certainly in contact with the plantar surface of the ball of the foot, but it is rather a support which is exempt from pain generating constraints, by virtue of the flexibility in the height of the anterior part and the contact with the ground only by the heel, which, added to holding the foot at a slope, realized by the heel compensated with inverted slope of the block sole, prohibits any forward shift of the weight of the body on the ball of the foot. Besides, this nonpainful support of the ball of the foot eliminates risks of the occurence of trophic troubles and considerably improves the equilibrium of the patient in the course of walking.

Complementarily, the heel on the block sole is compressible and presents a degree of compressibility which increases from the back toward the front, which allows a natural progression of the movements of the foot during walking.

Advantageously, the front part of the heel of the block sole is shaped into a wedge pointing toward the front of the shoe to confer on it the best possible foundation during the patient's movements.

Besides, a clearance is formed in the heel, between its wedge-shaped part and the anterior thin part of the block sole, and the base of this clearance is preferably situated slightly in the front of the flexion area of the sole, to avoid any blocking or crushing of the plantar arch, which without this provision would be a source of pain.

For obvious reasons of simplification of the manufacture of the shoe object of the invention, the heel and the thin anterior part of the block sole can advantageously be cast of one single piece, the increasing compressibility of the heel then resulting from the particular shape of the front part of this heel, as described above. If that would be insufficient, it would be possible to form air chambers in the heel of the block sole.

Besides, in the scope of research of a minimization of painful contact of the ball of the foot, the top side of the anterior part of the block sole presents a suitably positioned and dimensioned cutout to receive at least the bottom projection of the first metatarsal head of the foot, and such cutouts can also optionally be provided for the other metatarsal heads of the foot.

Preferably, the thin anterior part of the block sole will be beveled at the bottom of its front edge so that, if it is subject to an extreme accidental flexion, its risk of contact with the ground can be reduced maximally.

According to another important characteristic of the invention, the upper extends to the front of the shoe, and its walls rise along the edges of the anterior part of the block sole.

The shoe upper thus constitutes a supplementary protection, which particularly shelters the ball of the foot from the elements, without having to clamp it firmly and thus without subjecting it to painful constraints. In fact, the upper starts on the edge of the thin anterior part, i.e. at a good distance from the ball of the foot, at least from the part of the foot which is susceptible to pain.

The upper advantageously comprises two quarters of a flexible material, joined together at the back of the shoe and rising respectively along at least a part of the side edges of the block sole, and these quarters can be pulled away from each other to allow insertion of the foot into the shoe, by direct application of the plantar side of the foot on the bottom of the shoe, and can be connected to each other by one or more attachments.

By virtue of these arrangements, the patient can very easily introduce the foot into the upper of the shoe without any suffering.

Besides, by providing adjustable attachments, such as automatic attachment strips, loops or laces, to hold the two quarters of the upper together, one makes use of the possibility of independent clamping of the upper, at any point of the foot (posterior, median, anterior). Accordingly, it is possible to suitably tighten the posterior part of the upper around the back of the foot and simultaneously to realize a loose fastening of the anterior part, so as to confer maximum ease to the ball of the foot which is susceptible to pain, inside of the shoe.

Moreover, the adjustable attachments, on the balls of the feet affected by oedema, allow for following the variation of size of the oedema, particularly in the case of post-surgical oedemas.

A flexible tongue which can be raised is preferably affixed by a hinge-like connection along the front edge of the thin anterior part of the block sole and extends between the two quarters of the upper.

This tongue can be folded back between the two quarters of the upper before closing the attachments, which will then be applied on this tongue without coming into direct contact with the ball of the foot and thus without risking harming it under the effect of the tightening which the attachments exert thereon.

Alternatively, this protection of the ball of the foot from the effect of tightening the attachments can be obtained by a tongue extending laterally on the top free edge of one of the quarters of the upper, in the area of application of the attachments.

Besides, it is known that oedemas which are observed following surgical operations of the ball of the foot relate essentially to the big toe and that is why, according to another characteristic of the present invention, the thin anterior part of the block sole of the shoe which is the object is clearly more swelled out in its inside lengthwise half than in its outside lengthwise half. In other words, the inside part of the shoe is clearly more important than in traditional shoes.

Finally, it will also be suitable that the inside edge of the swelled inside lengthwise half of the thin anterior part is essentially parallel to the central lengthwise axis of this part, to avoid folding the big toe back toward the inside, as occurs in traditional shoes. This is particularly sought following operations for Hallux Valgus which represent approximately 80% of the cases of surgery on the ball of the foot.

One embodiment of the shoe according to the present invention will now be described in greater detail, but solely as a nonlimiting example, in reference to the attached drawings wherein:

FIGS. 3 and 4 are respectively a top view and a bottom view of this same shoe; and FIG. 5 is a section along line V—V of FIG. 1.

Figure 1:
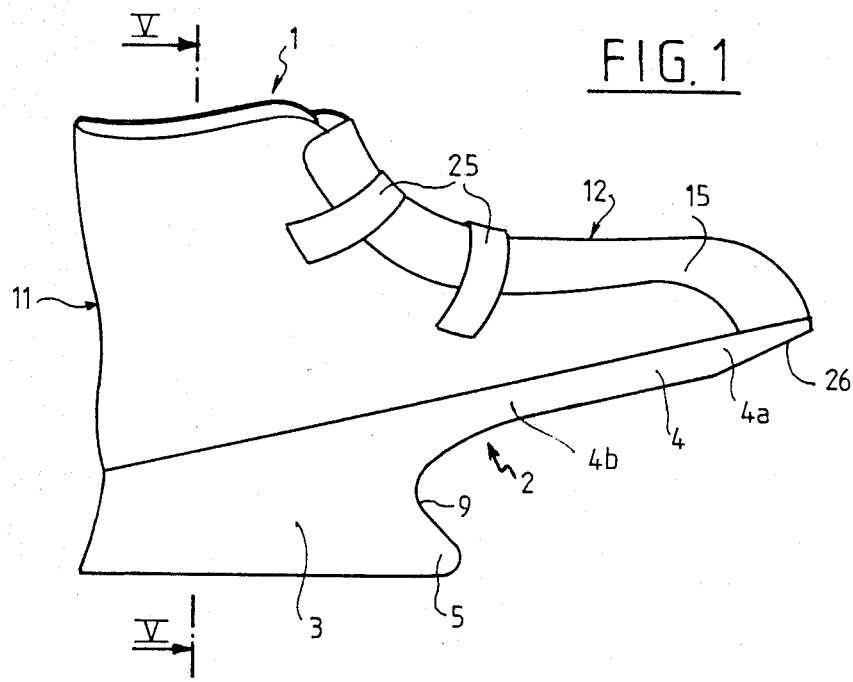
FIG. 1 is a side view of this shoe.

The shoe which is shown for post-surgical and post-trauma use is composed in a known manner of an upper 1 resting on a block sole 2 of which the posterior part is constituted of a heel 3 which is substantially thicker at the front than at the back, to give the shoe contact with the ground only at the heel.

According to the first characteristic of the invention, the block sole 2 also comprises a thin anterior part 4 which extends the top part of heel 3 forward while preserving the same upward inclination as the top part of the heel. Hereinafter the front areas 4a and the central area 4b of this thin anterior part 4 will respectively be called "pad" and "camber" by analogy with the traditional shoes.

Complementarily, in plan view, thin anterior part 4 of block sole 2 has larger dimensions than the corresponding dimensions of the foot and also is realized of a material which gives it a sufficient rigidity to confer on it a property of quasi-indeformability both lengthwise and crosswise. On the other hand, thin anterior part 4 is designed to be able to flex downward, in an area (arrow A of FIG. 2) situated essentially at the Lisfranc division of the foot.

Figure 2:
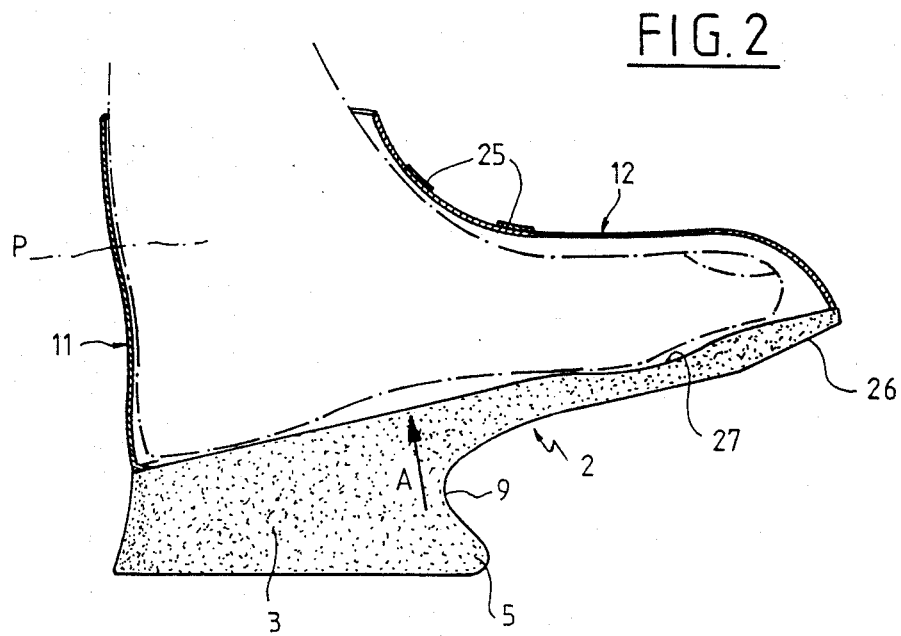
FIG. 2 is a lengthwise section of the shoe of FIG. 1, in place around the foot of a patient.

Heel 3 is compressible, with a degree of compressibility increasing from the back toward the front, and it will be observed in FIGS. 1 and 2 that its front part presents the shape of a wedge 5 directed toward the front of the shoe, so as to increase to the maximum the contact surface of block sole 2 with the ground.

Here it is important to note that wedge 5 of heel 3 and camber 4b of thin anterior part 4 between them define a clearance 9 of which the base on deepest point is situated slightly in front of the flexion area A of the thin anterior part.

Block sole 2 can advantageously be manufacctured by one single casting of a synthetic material possessing properties of elasticity and compressibility or by binding of several elements made of such a material. The variable compressibility of heel 3 will then result from the wedge configuration of the front part combined with the presence of clearance 9.

Upper 1 of the shoe comprises a posterior part 11 generally situated at the perpendicular of heel 3, and, according to another characteristic of the invention, upper 1 extends to the front of the shoe by an anterior part 12, intended to at least partially encase the ball of the foot of the patient without subjecting it to any constraint, and posterior part 11 of upper 1, as it is designed, conforms to the morphology of the foot of the patient, in order to clamp the back of the foot, which principally includes the tarsus and the heel, and to rise as far as the peroneotibial malleolus.

More precisely, upper 1 is formed totally of two lateral quarters 13 and 14 and a front tongue 15, all three manufactured of fabric, thick cloth or flexible leather.

FIG. 3 shows the two quarters 13 and 14 joined together at the back of the shoe by a line of vertical stitching 16 and rising along the lateral edges 17, 18 of block sole 2 (see FIG. 3), being stopped at a short distance from the front end point C of pad 4a.

FIG. 5 shows that the two quarters 13, 14 of upper 1 are actually folded back, at their bottom edge, and sewn under a lifting insole 19 on which is placed a cushion insole 20, and the shoe element which is thus formed is then combined with block sole 2, with insertion of a pad 21, for example by application of adhesive or by casting of this block sole in contact with said shoe element. Lifting insole 19 and cushion insole 20, which have not been shown in FIG. 2 for clarity of the drawing, have essentially the same width as top of block sole 2 and extend on approximately the entire length of the block sole.

Returning to FIG. 3, it is to be seen that tongue 15 is simply affixed along the portion, left free by the two quarters 13, 14, of the front edge of pad 4a of thin anterior part 4, by a line of stitching forming a hinge 22. The patient will then be able to easily raise tongue 15 to open upper 1, and having slightly pulled back quarters 13, 14, place the foot therein, without pain, by direct application of the plantar part of the foot on the cushion insole 20 of the shoe.

Then tongue 15 can be folded back on quarters 13, 14, and, in this position, it will be held in place by two automatic attachments such as "VELCRO" type tabs 25, provided on quarters 13, 14, at the instep.

It is to be noted here that these automatic attachments which are intended to hold the upper 1 around the foot make independent adjustment of the tightening of the upper possible at any point on the foot (posterior, median, anterior), thus allowing the upper to follow the local fluctuations of volume of the foot, which for example is due to a post-surgical oedema condition.

Once placed in the shoe while being immobilized at the back, the foot P of the patient will be held at a slight slope, in other words raised upward, and by virtue of the increasing compressibility of heel 3 of block sole 2, added to the flexibility of anterior part 4 at the point of the Lisfranc division, the patient will be able to walk normally without having the ball of the foot, which is subject to a painful wound or has just been operated on, come into contact with the ground. Of course, to do this, the maximum degree of clearance of pad 4a of thin anterior part 4 must be suitably adjusted by appropriate dimensioning of the front height of heel 3 and of the thickness of thin anterior part 4. In addition, the bottom line of the front edge of pad 4a will be beveled, as shown at 26 in FIGS. 1 and 2, to minimize risk of contact with the ground in case of an accidental excessive flexing.

In the course of walking, which can be done with a natural roll of the foot, the patient will retain good balance by virtue of the contact surface with the ground being enlarged at 5 of block sole 2 of the shoe. Furthermore, painful crushing down of the plantar arch will be avoided in the area of flexion A of anterior part 4 of block sole 2, because of the clearance 9.

The over-size of thin anterior part 4 will also protect the ball of the foot from lateral or front impacts which could perhaps induce great pain. Besides, althougn it is in contact with this anterior part 4 and completely surrounded by upper 1, which constitutes a supplementary protection, the ball of the foot will not be subjected to any painful constraints from these members, both because upper 1 encases it with a certain spacing and by its "unloading" resulting from the contact of the heel only, procured by heel 3 of block sole 2, as well as from the clamping of the back of the foot, assured by posterior part 11 of upper 1 and automatic attachments 25. Within the scope of this minimization of painful contact with the ball of the foot, the top side of pad 4a of anterior part 4 of block sole 2 will advantageously be provided with a cutout 27 which is of suitable position and dimensions to receive the bottom projection of the first metatarsal head and optionally the other metatarsal heads.

It is also to be noted that the support which generates no pain to the ball of the foot also allows the patient good equilibrium during walking and additionally prohibits trophic problems.

With reference to FIG. 4, some points will now be described concering the dimensions of pad 4a of thin anterior part 4 of block sole 2.

As is known, surgery carried out on the ball of the foot, followed by the formation of an oedema, generally affect the big toe. It is thus often enlarged and can wear an osteosynthesis pin projecting forward.

In the shoe object of the present invention, that is why the inside 28 of pad 4a, which is intended to support the big toe of the foot, is either of much larger dimensions than the external side 29 or is more swelled out at the front and on the side. In FIG. 4, that is shown by the fact that, on the one hand, the distance L between the inside edge 30 of pad 4a and the lengthwise central axis X of thin anterior part 4a is clearly greater than the distance l which separates this same axis X from the outside edge 31 of pad 4a, and that, on the other hand, the front end point C of the pad is offset toward the inside of axis X for a distance S.

Furthermore, the big toe which has been operated on or is affected by an oedema must keep its axis essentially parallel to that of the foot. To satisfy this requirement, the inside edge 30 of pad 4a of anterior part 4 of the block sole of the shoe according to the present invention is provided essentially parallel to the axis X of the sole.

Of course, remaining within the scope of the present invention, various adaptations or modifications may be applied to the shoe which has just been described. Thus, it is notable that the automatic attachments 25 can be replaced by loops or laces which also allow independent adjustment of the degree of tightness of the upper at different points on the foot.

Besides, upper 1 can be designed without front tongue 15 and, in this case, one of the two quarters 13 or 14 will be provided with a protective side tongue on which will be applied the automatic attachments 25 or the equivalent loops or laces, the instep thus being protected against the effects of tightening produced by these members.

Of course the dimensions of the shoe according to the invention will also be a function of the foot to be shod. As a concrete example, in size 37–38, block sole 2 will have a total length of approximately 245 mm on the top side, a height of 30 mm at the back and a height of 58 mm at the front in the plane of the end of wedge 5.

Finally, it will be added that the shoe in the example is a shoe for the right foot, and that a shoe for the left foot designed according to the principles of the invention, will present a plan view which is symmetrical with that of the right shoe.

I claim:

1. A shoe, particularly for a patient having surgery or injury to a ball of a foot, comprising:
   a block sole having a posterior part forming a compressible heel, said heel being substantially thicker at a front thereof that at a back thereof such that a top part of said heel is inclined upwardly and forwardly;
   a thin anterior part of said block sole extending forwardly from said top part of said heel and being inclined upwardly and forwardly similarly to said top part of said heel, said anterior part having transverse and longitudinal dimensions larger than corresponding dimensions of the foot and being substantially rigid in longitudinal and transverse directions while being flexible in height in a flexion area at the Lisfranc interline of the foot, dimensions of said heel and flexibility of said anterior part being a function of dimensions of the foot and preventing any contact of said anterior part with ground while standing and walking; and an upper integral with said block sole.

2. A shoe according to claim 1 wherein said heel has a degree of compressibility increasing from the back toward the front.

3. A shoe according to claim 1 wherein the front part of said heel is shaped in a wedge pointing toward a front of the shoe.

4. A shoe according to claim 3 wherein a clearance is formed in said heel between said wedge and said thin anterior part, said clearance having a base situated slightly in front of the flexion area.

5. A shoe according to claim 1 wherein said thin anterior part comprises a cutout on a top side thereof in position and of dimensions to receive at least a bottom projection of a first metatarsal head of the foot.

6. A shoe according to claim 5 wherein said thin anterior part is beveled at a bottom line of a front edge thereof.

7. A shoe according to claim 6 wherein an inside lengthwise half of said thin anterior part is more swelled out than an outside lengthwise half thereof.

8. A shoe according to claim 7 wherein an inside edge of the swelled inside lengthwise half of said anterior part is essentially parallel to a lengthwise axis of said anterior part.

9. A shoe according to claim 8 wherein the upper extends to a front of the shoe, and has walls rising along edges of said anterior part of the block sole.

10. A shoe according to claim 9 wherein the upper comprises two quarters of a flexible material joined together at the back of the shoe an rising respectively along at least a part of side edges of the block sole, said quarters can be pulled away from each other to allow insertion of the foot into the shoe, by direct application of a plantar side of the foot on a bottom of the shoe and can be connected to each other by at least one attachment.

11. A shoe according to claim 10 wherein a raisable flexible tongue is affixed by a connection forming a hinge along the front edge of said thin anterior part and extends between said two quarters of said upper.

12. A shoe according to claim 11 wherein one of said quarters comprises a protective tongue extending laterally on a top free edge thereof in an area of application of said attachment.

* * * * *